United States Patent
Mandish

(10) Patent No.: US 6,270,720 B1
(45) Date of Patent: Aug. 7, 2001

(54) SALT AIR FRESHENER APPARATUS AND METHOD

(76) Inventor: Theodore O. Mandish, 5055 State Road 46, Mims, FL (US) 32754

( * ) Notice: Subject to any disclaimer, the term of this patent is extended or adjusted under 35 U.S.C. 154(b) by 0 days.

(21) Appl. No.: 09/107,722

(22) Filed: Jun. 30, 1998

(51) Int. Cl.[7] .................................................... A62B 7/08
(52) U.S. Cl. ................................ 422/4; 239/60; 422/4; 422/5; 422/120; 422/123; 422/125
(58) Field of Search .................................. 422/4, 5, 120, 422/123, 125, 126, 306; 392/386, 387, 390, 393; 239/60; D23/366, 367; D11/131.1

(56) References Cited

U.S. PATENT DOCUMENTS

| | | | |
|---|---|---|---|
| 3,655,129 | * 4/1972 | Seiner | 239/60 |
| 4,051,159 | * 9/1977 | Tsoucalas et al. | 239/60 |
| 4,714,984 | * 12/1987 | Spector | 422/125 |
| 5,047,234 | * 9/1991 | Dickerson et al. | 239/60 |
| 5,572,800 | * 11/1996 | West | 34/97 |
| 5,651,942 | * 7/1997 | Christensen | 422/5 |
| 5,776,850 | * 7/1998 | Klatte et al. | 502/64 |
| 5,876,678 | * 3/1999 | Harrell et al. | 422/125 |

* cited by examiner

*Primary Examiner*—Krisanne Thornton
(74) *Attorney, Agent, or Firm*—William M. Hobby, III

(57) ABSTRACT

A salt sculpture air freshener is formed of a sodium chloride material, such as halite, formed into a sculpted shape and having a coated material thereover. It is mounted to a base having an electrical heater, such as an electric lamp, mounted therein for heating the coated salt material. The salt material may have a light tunnel therethrough for passing the heat and light from the electric heater so that the coated material is heated to reduce airborne microbiological agents adjacent thereto and to freshen the air therearound. The process of making an air freshener includes forming the salt material into a sculpted shape, selecting and coating the formed salt material with a coating material having bactericidal properties, mounting the coated salt material to a base having a heater therein, and heating the salt material to reduce airborne microbiological agents adjacent thereto and to freshen the air therearound.

15 Claims, 2 Drawing Sheets

SALT AIR FRESHENER APPARATUS AND METHOD

BACKGROUND OF THE INVENTION

The present invention relates to an apparatus and method of making an air freshener and to an air freshener made of a coated pre-cast or sculpted salt (NACL) material.

Halite is a colorless or white material made up predominately of sodium chloride (NACL) which occurs in cubic crystals and is found in dried lake beds and arid climates and which is used as common table salt. Halite is sometimes called rock salt and has been mined in the historic mines in Poland. Translucent halite, as found in Poland, may have impurities therein which form various colors including orange, rose, and red built into the mineral structures of the crystals by the high concentration of natural trace elements, such as hematite, manganese, iodine, copper, iron and zinc. Halite has been mined in Poland for several hundred years and the mines are among the oldest mines in the world. The salts extracted from the mines have been sold worldwide as healing salts and many metaphysical properties have been claimed for the salt. It has been shown that when halite is heated, negative ions are produced within an enclosed room and in the area surrounding the heated halite crystal. It has also been shown that an ion atmosphere will reduce dust and the bacterial count in the air. Halite crystals have been used in the past for various types of salt sculptures and have also been used as lighted sculptures.

The present invention is directed towards an improvement in salt sculptures made of a crystalline halite which has been coated with a predetermined coating material to form a decorative sculpture which, when heated with an electric lamp or other heater, will reduce airborne microbiological agents in the room where the precast salt composite sculpture is being heated and freshens the air in a room.

Prior art air fresheners can be seen in the Gyulay U.S. Pat. No. 4,647,428, for a room air freshener which is in the form of a porous ceramic ring in combination with an upright positioned light bulb. The ring has a premeasuring cavity so that a fragrance generating liquid filling the cavity will be completely absorbed by the ceramic ring. The liquid will be vaporized when the ring is placed on a light bulb. The Spector U.S. Pat. No. 4,346,059, teaches an aroma generating lamp structure which has an electric bulb mounted on a base and enclosed by a shell which is partially translucent. The base has a bottle filled with a liquid scent mounted thereto and allows the liquid to be sprayed onto an absorbent pad where it is vaporized by the heat of the light bulb. The Cloud U.S. Pat. No. 2,757,278, combines an ozone lamp and vaporizer for producing ozone and vaporizing a chemical, such as triethylene glycol, for the control of odor, germs, and bacteria and in the vaporization of chemicals, such as hexachloride, for the control of insects. The Hasegawa et al. U.S. Pat. No. 5,290,546, shows a cordless thermal vaporizer of a liquid in which the body of the vaporizer has a heater for heating a wick for drawing up a chemical solution from a bottle. The vaporizer attaches directly to an electrical outlet. The Hoyt et al. U.S. Pat. No. 5,014,913, teaches an air freshening device which has an air freshener fluid container having a wick and has an outer closure support for the container using a pair of adjustable closure half shells. The Feit U.S. Pat. No. 4,285,905, shows a method and article for dispersing a volatile compound in an environment. The Pozzo U.S. Pat. No. 5,069,877, is an article for diffusing volatile substances, such as perfume. In the prior patent to Gebauer et al., U.S. Pat. No. 4,842,853, a solid contains a fragrance substance and/or disinfectant and at least one sublimable substance. When the solid is exposed to the environment, it releases a fragrance substance to act as a disinfectant.

The aim of the present invention is produce a decorative halite sculpture which when heated, such as by an electric lamp, lights the sculpture and freshens the surrounding air and reduces airborne microbiological agents. The coated halite material can be recoated after a period of use and the supporting base for the sculpture can have an additional trough for vaporizing additional disinfectant chemicals. It is also an aim to produce a solid cast cementuous object which can be used in freshening and purifying the air.

SUMMARY OF THE INVENTION

A salt sculpture air freshener is formed of a sodium chloride or salt composite material, such as by precasting or molding, having a coating material thereover. It is mounted to a base having an electrical heater, such as an electric lamp, mounted therein for heating the coated salt material. The salt material may have a light tunnel therethrough for passing the heat and light energy from the electric heater so that the coated material is heated to reduce airborne microbiological agents adjacent thereto and to freshen and purify the air therearound. The process of making an air freshener includes forming the salt material into a sculpted shape, selecting and coating the formed salt material with a coating material having bactericidal properties, mounting the coated salt material to a base having a heater therein, and heating the salt material to reduce airborne microbiological agents adjacent thereto and to freshen the air therearound.

BRIEF DESCRIPTION OF THE DRAWINGS

Other objects, features, and advantages of the present invention will be apparent from the written description and the drawings in which.

DESCRIPTION OF THE PREFERRED EMBODIMENT

Figures 1, 2:
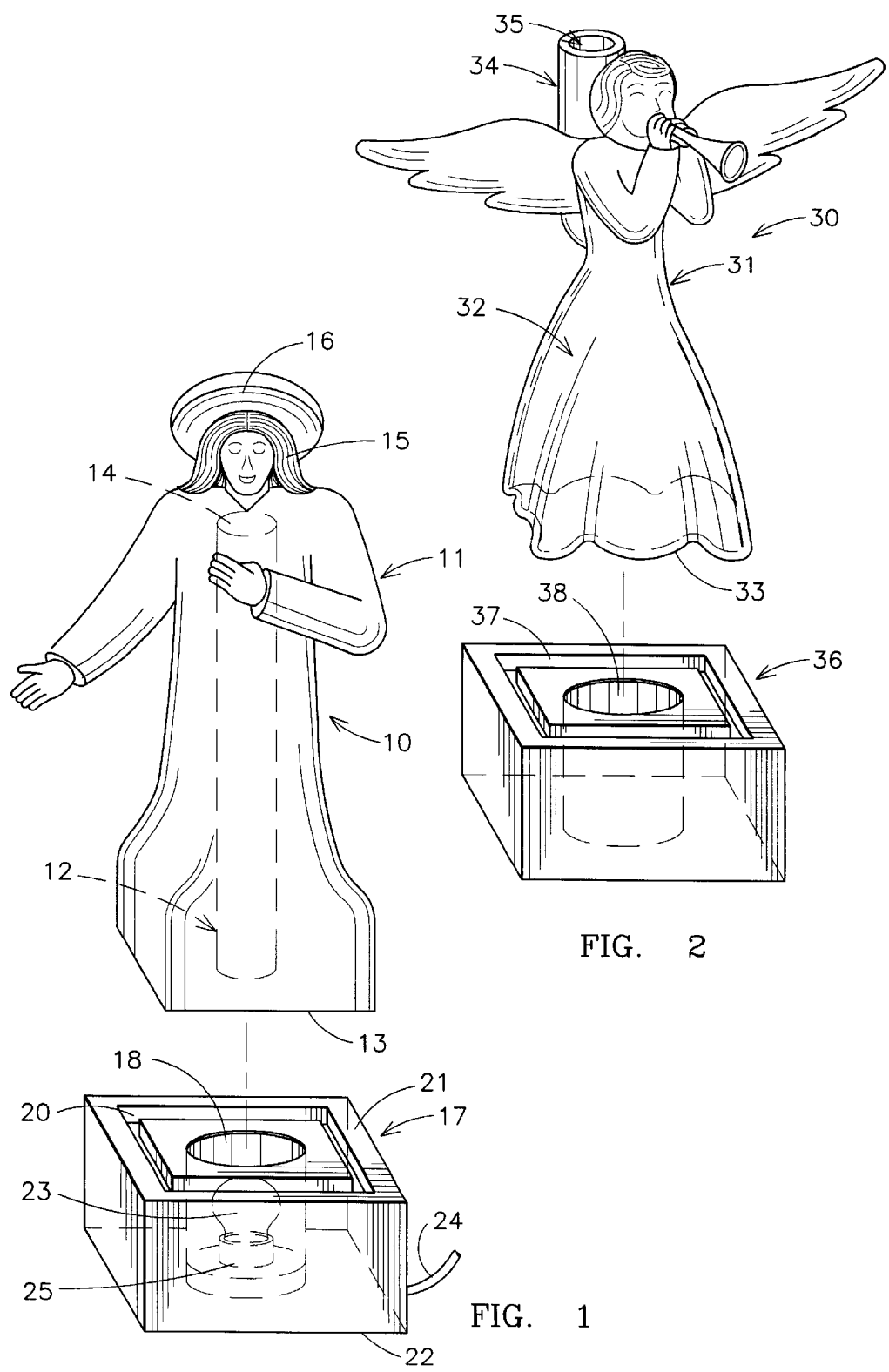
FIG. 1 is an exploded view of a decorative sculpture air freshener and purifier in accordance with the present invention.
FIG. 2 is a perspective view of a second embodiment of a decorative sculpture in accordance with the present invention.

Referring to FIG. 1 of the drawings, an exploded view of the decorative sculptured air freshener 10 has a sculpture 11 formed of a salt (sodium chloride) material, such as halite or a salt composite material. The salt sculpture 11 has a bore 12 extending from the bottom 13 thereof up to a point 14 just below the head 15 of the figure. The head 15 of the sculpture 11 has a glass or plastic halo 16 mounted thereto. The bore 12 is for the passage of heat and light energy therethrough for both heating and lighting the sculpture 11 and also lighting the halo 16 from a lamp in the base. A base 17 has a bore 18 extending therethrough and has a trough 20 formed into the top portion 21 thereof and aligned so that the sculpture 11 mounts to the base 17 inside of the surrounding trough 20. The base has a bottom 22 for setting on a surface and has an electric lamp 23 mounted in the opening 18. It will, of course, be clear that the lamp can be mounted beneath the base 17 and can also include other types of heaters, such as an electrical resistance heating wire. An electrical conductor 24 is connected through the base to the electric lamp 23 base 25 and is used to power the electric light 23 which acts as both the heater and light source for lighting the salt sculpture 11 and the glass or plastic halo 16. The salt sculpture 11 is coated with a disinfectant, such as M22, a disinfectant chemical sold by Cape Kennedy Plastics, Inc. Chemical Division, Mims, Fla. and derived from citrus which has been found to act as a microbiologicalcide.

In operation, the salt sculpture, which has been coated and mounted on the base 17, has the heater 23 actuated to heat the sculpture as well as the base and trough 20 which may include an additional source of M22 vapor. The halite or salt composite produces negative ions in the air while also vaporizing a disinfectant which combined actions produce a reduction of the microbiological agents in the air including both bacteria and fungi which are airborne in dust or the like while cleaning and deodorizing the air surrounding the sculpture 11 and in the room where the statute has been placed. It should be understood that the sculpture 11 can be a precast or molded sculpture of a salt composite material which composite can be sodium chloride having copper, iron, magnesium and a disinfectant chemical mixed therewith.

Turning now to FIG. 2, a second embodiment of an air freshener and purifier 30 is illustrated having a sculptured salt composite material 31 in the shape of an angel having a hollowed out chamber 32 open in the bottom end 33. The angel includes a reservoir 34 having an opening 35 for the addition of a disinfectant or deodorizing chemical, such as M22. The salt sculpture 31 is also coated with the M22 and is mounted to the base 36 having a trough 37 and a bore 38 extending therethrough. The salt sculpture 31 thus may be coated with a coating material which is also supported in a reservoir 34 and which may have the coating material placed in the trough 37. A lamp or other electrical heating source may be placed in the base or under the base for producing heat for generating ions from the salt material as well as vaporizing the disinfectant liquid placed in the reservoir 34, the trough 37, and coating the salt sculpture 31.

The method of making and using the air freshener and purifier, as illustrated in FIGS. 1 and 2, includes forming a halite or other salt material, formed principally of sodium chloride, into a precast or sculpted shape 11 or 31 and selecting a coating material, such as M22, for coating the salt sculpture 11 or 31 and for adding to the base troughs 20 or 37 and to the reservoir 34 and attaching the salt sculpture forms 11 and 31 to the base 17 or 36. The base includes the mounting of an electrical or other heater thereto, such as the electric lamp 23, which is positioned to light and heat the salt sculpture 11 and 31 to produce negative ions in the air as well as to vaporize the coating chemicals. A glass or plastic halo 16 may be placed on the salt sculpture 11 to enhance the lighted image.

Figure 3:
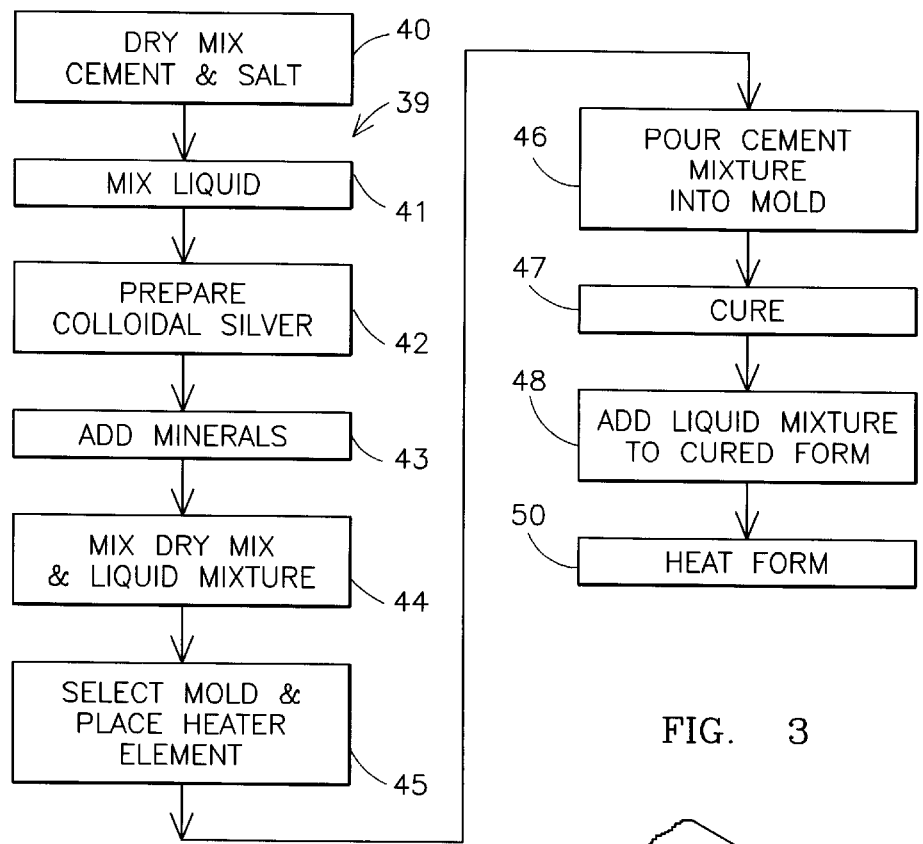
FIG. 3 is a flow diagram of a process for making an air freshener.

Turning to FIG. 3, a flow diagram 39 of an alternate process for making an air freshener is illustrated. A dry cement is mixed with sodium chloride (NACL) or salt as a first step 40 in the process. The mixture includes 40% or more by volume of table sodium chloride to form a dry composite mix of salt and cement. A liquid is formed at 41 which includes the use of a citrus extract, glycerin, propylene glycol, and may have water and other inert materials added to the liquid mix. A second liquid of colloidal silver is formed at 42. To prepare the colloidal silver, distilled water is heated to boiling in a glass container and silver wires are immersed in the water. An electric source is attached to the silver wires for 20 minutes to produce from 3–5 parts per million of silver in the solution. The colloidal silver solution may have other minerals added at 43 including copper and iron which, when added to the colloidal silver solution, enhances the production of negative ions. The dry mix from step 41 and the liquid mix formed in steps 41, 42, and 43 are mixed together at 44 to form a cement composite slurry. A mold is selected at 45 which has had a resistance heating element or wire placed within the mold and protruding therefrom. The slurry is poured at 46 into the selected mold having the heater element therein and is cured at 47 to form a molded object, such as a sculpture of FIGS. 1 and 2, or the base of the sculptures formed with a trough therein to hold the liquid. In the case of a mold trough, the liquid mixture of step 41 can be added to the trough at 48 or the sculpture can be coated with the liquid mixture. A heating element formed in the cured object can be connected to an electrical source and actuated at 50 to heat the formed object and also to heat the liquid added thereto. Once heated, the form and the liquid create negative ions within the surrounding atmosphere which, in combination with the liquid vapor, freshens the surrounding air and reduces airborne microbiological agents.

Figure 4:
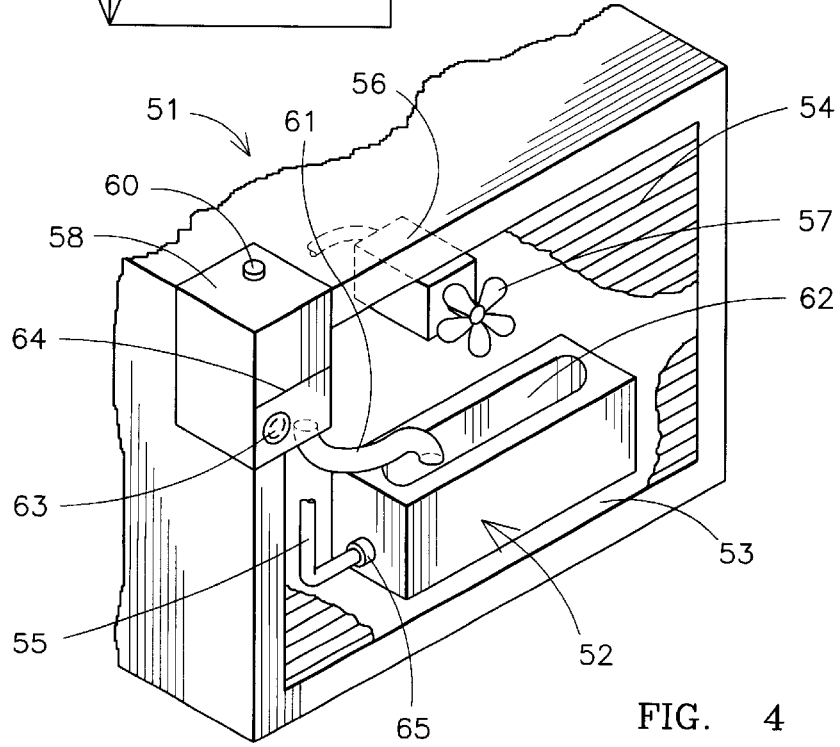
FIG. 4 is a partial perspective of an air conditioning system having an air freshener and purifier in accordance with the present invention.

Turning to FIG. 4, another embodiment of the present invention is shown installed in an air conditioner unit 51 which has the formed object of the process of FIG. 3 in the nature of a solid trough 52 placed on a base 53 of the air conditioning unit 51. The air conditioning unit 51 also has a grill and filter 54 placed in front of the mounted trough 52. The cement and sodium chloride (salt) trough 52 has a heating element electric wires 55 extending therefrom and connected to the same source as the fan motor 56 which drives a fan 57 so that any time the fan is actuated in the air conditioner 51, the heating elements within the trough 52 are actuated. A container 58 for the liquid mix from steps 41, 42, and 43 has a filler cap 60 therein and a tube 61 leading therefrom into the trough basin 62. A timer 63 actuates a valve 64 to release additional liquid into the trough 62 as needed. When the air conditioner 51 is being operated, the fan 57 is cycled on to blow air over the cooling coils and over the cement salt container 52 and over the liquid in the trough 62. This creates an ionized atmosphere and reduces microbiological agents in the air. The heating elements 65 can be seen on the edge of the form 52 and can be a sealed corrosive resistant chromolox heating element or wire. The liquid being fed into the trough 62 can be a mixture of water, citrus extract, colloidal silver, and iron mixed in accordance with the process of FIG. 3.

It should be clear at this time that the method and apparatus for using an air freshener and purifier and especially to an air freshener which reduces airborne microbiological agents while producing a decorative and aesthetically pleasing desk sculpture has been provided. In addition, it will be clear that a process of making an air freshener and purifier in a solid cementuous object has been provided which can be operated in an air conditioning system. However, the present invention is not to be considered limited to the forms shown which are to be considered illustrative rather than restrictive.

I claim:

1. A process of making and using an air freshener and purifier comprising the steps of:

forming a sodium chloride material into a sculpted shape;

selecting a coating material for said formed sodium chloride material;

coating said formed sodium chloride material with said predetermined coating material;

selecting a base for mounting said sodium chloride material thereon;

mounting said formed sodium chloride material to said selected base; and heating said formed and coated sodium chloride material to thereby reduce airborne microbiological agents adjacent thereto.

2. A process of making and using an air freshener in accordance with claim 1 in which the step of coating said formed sodium chloride material includes coating said formed sodium chloride material with a citrus extract.

3. A process of making and using an air freshener in accordance with claim 1 in which the step of forming a sodium chloride material includes forming a sodium chloride material into a sculpted block of crystalline halite.

4. A process of making and using an air freshener in accordance with claim 3 in which the step of selecting a base includes selecting a base having a trough formed therein around the area for mounting said formed sodium chloride material.

5. A process of making and using an air freshener in accordance with claim 1 in which the step of forming a sodium chloride material includes forming a sodium chloride material into a sculpted shape having a light tunnel extending thereinto.

6. A process of making and using an air freshener in accordance with claim 5 including the step of mounting an electric heater in said base.

7. A process of making and using an air freshener in accordance with claim 5 including the step of mounting an electric lamp in said base.

8. A process of making and using an air freshener in accordance with claim 7 including the step of mounting a transparent member to said formed sodium chloride material located above said light tunnel and lighted by said electric lamp in said base directing light through said light tunnel.

9. A sodium chloride air freshener comprising:

a sodium chloride material formed into a sculpted shape and having a coating material thereover;

a base having said coated sodium chloride material mounted thereon; and an electrical heater mounted to said base for heating said coated sodium chloride material whereby the coated sodium chloride material can be heated to reduce airborne microbiological agents adjacent thereto and freshen the air therearound.

10. A sodium chloride air freshener in accordance with claim 9 in which sodium chloride material coating is a citrus extract.

11. A sodium chloride air freshener in accordance with claim 9 in which said sodium chloride material is a decorative block of crystalline halite.

12. A sodium chloride air freshener in accordance with claim 11 in which said base has a trough formed therein around the area for mounting said sodium chloride material.

13. A sodium chloride air freshener in accordance with claim 9 in which said sodium chloride material has a light tunnel extending thereinto above said base.

14. A sodium chloride air freshener in accordance with claim 13 in which said electric heater is an electric lamp mounted in said base.

15. A sodium chloride air freshener in accordance with claim 14 in which a transparent member is attached to sodium chloride material above said light tunnel in said sodium chloride material, whereby said transparent material is lighted by said electric lamp in said base directing light through said light tunnel.

* * * * *